(12) United States Patent
Sachdeva et al.

(10) Patent No.: US 12,233,043 B1
(45) Date of Patent: Feb. 25, 2025

(54) METHOD OF TRANSDERMAL DELIVERY OF CANNABINOID COMPOSITIONS

(71) Applicant: Florida A&M University, Tallahassee, FL (US)

(72) Inventors: Mandip Sachdeva, Tallahassee, FL (US); Arvind Bagde, Tallahassee, FL (US); Oluwasevi Salau, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 332 days.

(21) Appl. No.: 17/862,957

(22) Filed: Jul. 12, 2022

(51) Int. Cl.
| | | |
|---|---|---|
| A61K 31/352 | (2006.01) | |
| A61K 9/00 | (2006.01) | |
| A61K 9/06 | (2006.01) | |
| A61K 31/05 | (2006.01) | |
| A61P 29/00 | (2006.01) | |

(52) U.S. Cl.
CPC .......... A61K 31/352 (2013.01); A61K 9/0014 (2013.01); A61K 9/06 (2013.01); A61K 31/05 (2013.01); A61P 29/00 (2018.01)

(58) Field of Classification Search
CPC ...... A61K 31/352; A61K 9/0014; A61P 29/00
USPC .......................................................... 514/454
See application file for complete search history.

(56) References Cited

U.S. PATENT DOCUMENTS

| 10,588,871 | B1 * | 3/2020 | Fracassi | A61K 47/36 |
| 2012/0202891 | A1 * | 8/2012 | Stinchcomb | A61K 47/08 |
| | | | | 514/733 |
| 2013/0184354 | A1 | 7/2013 | Jackson et al. | |
| 2016/0256411 | A1 * | 9/2016 | Aung-Din | A61P 25/28 |
| 2019/0216870 | A1 | 7/2019 | Witowski et al. | |
| 2020/0345657 | A1 * | 11/2020 | Lurya | A61K 36/21 |
| 2021/0315837 | A1 * | 10/2021 | Murphy | A61K 36/185 |

FOREIGN PATENT DOCUMENTS

EP 2444081 A1 4/2012

OTHER PUBLICATIONS

Crippa, J.A. et al. Translational Investigation of the Therapeutic Potential of Cannabidiol (CBD): Toward a New Age. Frontiers in Immunology, Sep. 21, 2018. vol. 9, Article 2009. doi:10.3389/fimmu.2018.02009.
Lodzki, M. et al. Cannabidiol—transdermal delivery and anti-inflammatory effect in a murine model. Journal of Controlled Release, 93 (2003), 377-387. doi:10.1016/j.jconrel.2003.09.001.
Stinchcomb, A.L. et al. Human skin permeation of delta8-tetrahydrocannabinol, cannabidiol and cannabinol. Journal of Pharmacy and Pharmacology, 2004, 56: 291-297.
Pastore, M.N. et al. Transdermal patches: history, development and pharmacology. British Journal of Pharmacology (2015) 172, 2179-2209. doi:10.1111/bph. 13059.
Tijani, A.O. et al. Delivering therapeutic cannabinoids via skin: Current state and future perspectives. Journal of Controlled Release, 334 (2021), 427-451. doi:10.1016/j.jconrel.2021.05.005.
Koch, N. et al. Cannabidiol aqueous solubility enhancement: Comparison of three amorphous formulations strategies using different type of polymers. International Journal of Pharmaceutics, 589 (2020), 119812.

* cited by examiner

*Primary Examiner* — Jeffrey H Murray
*Assistant Examiner* — Rilla Marie Samsell
(74) *Attorney, Agent, or Firm* — Michele L. Lawson; Smith & Hopen, P.A.

(57) ABSTRACT

A composition, method of treating inflammation or edema, and method of increasing transdermal permeation and flux of at least one cannabinoid is presented. The composition is comprised of at least one cannabinoid, at least one permeation enhancer and at least one hydrophilic polymer. Administration of a therapeutically effective amount of this composition of can be used to treat both inflammation and edema in a patient as well as increasing transdermal permeation and flux of the at least one cannabinoid.

14 Claims, 9 Drawing Sheets

METHOD OF TRANSDERMAL DELIVERY OF CANNABINOID COMPOSITIONS

FIELD OF INVENTION

This invention relates to compositions and methods of treatment for inflammation and edema. Specifically, the invention provides compositions comprised of cannabinoid compounds and permeation enhancers which increase transdermal permeation of the compounds as well as methods of treatment using such for inflammation and edema.

BACKGROUND OF THE INVENTION

Over the years, clinical and preclinical studies have demonstrated the therapeutic significance of cannabinoids for diverse indications including schizophrenia, chronic pain, chemotherapeutic induced neuropathic pain, sickle cell disease and Huntington's disease (Crippa, Guimarães et al. 2018, Tijani, Thakur et al. 2021). For transdermal drug delivery, ideally API should have low molecular weight (<1000 Da), affinity towards lipophilic and hydrophilic phases, short half-life and low melting point. CBD, CBG and THCV have molecular weight <400 Da, melting point of 66-67° C., log p values of >5 which makes them highly lipophilic (Tijani, Thakur et al. 2021). However, they are insoluble in water (2-10 µg/ml in water) (Koch, Jennotte et al. 2020). Because of high lipophilicity, they tend to retain more in the lipophilic epidermal region (stratum corneum) compared to hydrophilic dermal region which prevents their systemic absorption (Tijani, Thakur et al. 2021).

Few researchers have worked on improving the systemic absorption of cannabinoids including Jiri et al who patented different CBD formulations including aerosol, emulgel and ointment and evaluated them on human subjects for the treatment of inflammatory diseases (Skalicky, Husek et al. 2012). Jackson et al also patented CBD formulation with no IVPT results (Jackson and Hyatt 2013). Lowe et al formulated and patented transdermal CBD formulation by solubilizing it in volatile oils (*eucalyptus* oil and emu oil) with no in vitro or in vivo data (Tijani, Thakur et al. 2021). Similarly, employment of oils: sunflower, mineral and argan for improving the transdermal delivery of CBD has been reported in the literature (Tijani, Thakur et al. 2021). However, all these studies lack characterization of formulation including flux determination which is important to know the drug permeation profile across the skin after application of the formulation.

Lodzki et al developed a reservoir system for transdermal delivery of CBD using ethosomal carriers, in which they achieved ~110.07 µg/cm$^2$ CBD permeation in abdominal skin, ~11.54 µg (µg/g muscle) in abdominal muscle and ~0.67 µg/ml concentration in the systemic circulation in their in vivo study in mice (Lodzki, Godin et al. 2003). However, API may leak out from the reservoir patch as reported for fentanyl patch and may affect the systemic absorption of API (Pastore, Kalia et al. 2015).

Stinchcomb et al. who developed the cannabinoids solutions in propylene glycol, water and ethanol combination showed flux of Δ8-tetrahydrocannabinol (Δ8-THC), CBD and cannabinol (CBN) in 48 hrs IVPT study. Their IVPT results showed maximum flux of ~1.47 µg/cm$^2$/hr CBD permeation and cumulative amount of ~78.61 µg CBD permeation at the end of 48 hrs (Stinchcomb, Valiveti et al. 2004).

Witowski et al patented transdermal encapsulated cannabinoid formulation (patent no. LU101384) in which they achieved flux of 2.7 µg/cm$^2$/hr for CBD formulation in 72 hrs in vivo study (Witowski and Salm 2020). Overall, there is a limited literature available on transdermal delivery of cannabinoids (Tijani, Thakur et al. 2021).

In light of the limited treatment options for transdermal delivery of cannabinoids, what is needed is a novel transdermal cannabinoid delivery treatment capable of overcoming the shortcomings of the prior art.

SUMMARY OF INVENTION

The inventors have developed a method of increasing the transdermal permeation of cannabinoids, such as cannabidiol (CBD), cannabigerol (CBG) and tetrahydrocannabivarin (THCV), using a chemical permeation enhancer approach. The inventors evaluated the compositions for their anti-inflammatory effect in vivo in a paw edema model in rats. Transdermal gel formulations of cannabinoids were developed using FDA approved inactive ingredients: lactic acid (LA), polyethylene glycol-400 (PEG-400), N-methyl-2 pyrrolidone (NMP), dimethyl sulfoxide (DMSO). In vitro skin permeation testing (IVPT) showed flux of at least ~8.50 µg/cm$^2$/hr for CBD, ~6.00 µg/cm$^2$/hr for CBG, and ~33.00 µg/cm$^2$/hr for THCV for 0-72 hours (hrs). Additionally, IVPT study showed cumulative drug permeation of at least about 610.96±88.92 g/cm$^2$, 432.09±35.59 µg/cm$^2$ and 2384.44±42.22 µg/cm$^2$ from CBD, CBG and THCV gel formulations, respectively. Further, effect of excipients on cannabinoid permeation showed that, formulations containing lactic acid, NMP and DMSO showed significantly (p<0.0001) enhanced flux of cannabinoids as compared to formulation without LA, NMP and DMSO. In vivo studies showed that paw edema was significantly (p<0.0001) reduced in the groups containing CBD, CBG, THCV as compared to control (no treatment). As such, flux of CBD, CBG and THCV was significantly enhanced using chemical permeation enhancers approach which helped in reducing rat paw edema.

In an embodiment, a method of treating inflammation or edema in a patient in need thereof is presented comprising administering a therapeutically effective amount of a composition to the patient in need thereof. The composition comprises at least one cannabinoid, at least one permeation enhancer and at least one hydrophilic polymer, wherein the administration of the composition treats the inflammation or edema of the patient. The composition may be a hydrogel.

The at least one cannabinoid may be selected from the group consisting of Tetrahydrocannabivarin (THCV), Cannabidiol (CBD), Cannabichromene (CBC), Cannabigerol-monomethylether (CBGM), Delta-8-tetrahydrocannabinol (delta 8-THC), Delta-9-tetrahydrocannabinol (THC), Cannabigerol (CBG), Cannabinol (CBN), bibenzyl(−)-cis-perrottetinene (cis-PET), and combinations thereof. In some embodiments, the at least one cannabinoid is CBD, CBG, or THCV.

The at least one permeation enhancer may be selected from the group consisting of lactic acid (LA), polyethylene glycol-400 (PEG-400), N-methyl-2 pyrrolidone (NMP), dimethyl sulfoxide (DMSO), and combinations thereof. In some embodiments, the at least one permeation enhancer is the combination of LA, NMP, and DMSO.

The at least one hydrophilic polymer may be selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof.

In an embodiment, a composition for treating inflammation in a patient in need thereof is presented comprising at least one cannabinoid; at least one permeation enhancer; and at least one hydrophilic polymer. The composition may be a hydrogel.

The at least one cannabinoid may be selected from the group consisting of Tetrahydrocannabivarin (THCV), Cannabidiol (CBD), Cannabichromene (CBC), Cannabigerolmonomethylether (CBGM), Delta-8-tetrahydrocannabinol (delta 8-THC), Delta-9-tetrahydrocannabinol (THC), Cannabigerol (CBG), Cannabinol (CBN), bibenzyl(-)-cis-perrottetinene (cis-PET), and combinations thereof. In some embodiments, the at least one cannabinoid is CBD, CBG, or THCV.

The at least one permeation enhancer may be selected from the group consisting of lactic acid (LA), polyethylene glycol-400 (PEG-400), N-methyl-2 pyrrolidone (NMP), dimethyl sulfoxide (DMSO), and combinations thereof. In some embodiments, the at least one permeation enhancer is the combination of LA, NMP, and DMSO.

The at least one hydrophilic polymer may be selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof.

In a further embodiment, a method of increasing transdermal permeation of at least one cannabinoid through a skin of a patient in need thereof is presented comprising administering a therapeutically effective amount of a composition to the patient in need thereof, wherein flux of the at least one cannabinoid is increased above a control within about 72 hours after administration of the composition. The increase in the flux increases the transdermal permeation of the at least one cannabinoid. In some embodiments, the increase in flux is to at least about 5.00 μg/cm$^2$/hr or at least about 6.00 μg/cm$^2$/hr. The composition comprises at least one cannabinoid; at least one permeation enhancer; and at least one hydrophilic polymer.

The at least one cannabinoid may be selected from the group consisting of Tetrahydrocannabivarin (THCV), Cannabidiol (CBD), Cannabichromene (CBC), Cannabigerolmonomethylether (CBGM), Delta-8-tetrahydrocannabinol (delta 8-THC), Delta-9-tetrahydrocannabinol (THC), Cannabigerol (CBG), Cannabinol (CBN), bibenzyl(-)-cis-perrottetinene (cis-PET), and combinations thereof. In some embodiments, the at least one cannabinoid is CBD, CBG, or THCV.

The at least one permeation enhancer may be selected from the group consisting of lactic acid (LA), polyethylene glycol-400 (PEG-400), N-methyl-2 pyrrolidone (NMP), dimethyl sulfoxide (DMSO), and combinations thereof. In some embodiments, the at least one permeation enhancer is the combination of LA, NMP, and DMSO.

The at least one hydrophilic polymer may be selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof.

BRIEF DESCRIPTION OF THE DRAWINGS

For a fuller understanding of the invention, reference should be made to the following detailed description, taken in connection with the accompanying drawings, in which:

FIG. 2A-D are a series of images depicting (A) IVPT study showing cumulative drug permeation from gel formulation at the end of 72 hrs., (B) In vitro skin deposition study showing CBD deposition from gel formulation at the end of 72 hrs., (C) IVPT study showing cumulative drug permeation from gel formulation at 24, 48 and 72 hrs.(D) IVPT study showing CBD flux from gel formulation at 24, 48 and 72 hrs.

FIG. 3A-D are a series of images depicting (A) IVPT study showing cumulative drug permeation from gel formulation with and without PEG-400 and Lactic acid at the end of 72 hrs., (B) IVPT study showing cumulative drug permeation from gel formulation with and without PEG-400 and Lactic acid at 24, 48 and 72 hrs.(C) IVPT study showing CBD flux from gel formulation with and without PEG-400 and Lactic acid at 24, 48 and 72 hrs., (D) In vitro skin deposition study showing CBD deposition from gel formulation with and without PEG-400 and Lactic acid at the end of 72 hrs.

FIG. 4A-D are a series of images depicting (A) IVPT study showing cumulative drug permeation from gel formulation with and without NMP and DMSO at the end of 72 hrs (B) IVPT study showing cumulative drug permeation from gel formulation with and without NMP and DMSO at 24, 48 and 72 hrs (C) IVPT study showing CBD flux from gel formulation with and without NMP and DMSO at 24, 48 and 72 hrs (D) In vitro skin deposition study showing CBD deposition from gel formulation with and without NMP and DMSO at the end of 72 hrs.

FIG. 5A-D are a series of images depicting (A) IVPT study showing cumulative drug permeation from gel formulation with gelling agent concentration of 1, 2.5 and 5% at the end of 72 hrs., (B) IVPT study showing cumulative drug permeation from gel formulation with gelling agent concentration of 1, 2.5 and 5% at 24, 48 and 72 hrs.(C) IVPT study showing CBD flux from gel formulation with gelling agent concentration of 1, 2.5 and 5% at 24, 48 and 72 hrs., (D) In vitro skin deposition study showing CBD deposition from gel formulation gelling agent concentration of 1, 2.5 and 5% at the end of 72 hrs.

FIG. 6A-D are a series of images depicting (A) IVPT study showing cumulative drug permeation from CBG and THCV gel formulation at the end of 72 hrs., (B) IVPT study showing cumulative drug permeation from CBG and THCV gel formulation at 24, 48 and 72 hrs., (C) IVPT study showing CBG and THCV flux from gel formulation at 24, 48 and 72 hrs.,(D) In vitro skin deposition study showing CBG and THCV deposition from gel formulation at the end of 72 hrs.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Abbreviations

API—Active Pharmaceutical Ingredient
CBC—Cannabichromene
CBD—Cannabidiol
CBG—Cannabigerol
CBGM—Cannabigerol-monomethylether
CBN—Cannabinol
Cis-PET—bibenzyl(-)-cis-perrottetinene
Delta 8 THC—Delta-8-tetrahydrocannabinol
EC—ethylcellulose
HEC—hydroxyethyl cellulose
HEMC—hydroxyethyl methylcellulose
HPC—hydroxypropyl cellulose
HPMC—hydroxypropyl methylcellulose
IVPT—In Vitro Permeation Testing
MC—methylcellulose
THC—Tetrahydrocannabinol
THCV—Tetrahydrocannabivarin Definitions As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

Where a range of values is provided, it is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed in the invention. The upper and lower limits of these smaller ranges may independently be excluded or included within the range. Each range where either, neither, or both limits are included in the smaller ranges are also encompassed by the invention, subject to any specifically excluded limit in the stated range. Where the stated range includes one or both of the limits, ranges excluding either or both of those excluded limits are also included in the invention.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, "about" means approximately or nearly and in the context of a numerical value or range set forth means±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein "patient" or "subject" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include humans, rodents, mammals, aquatic mammals, domestic animals such as dogs and cats, and farm animals such as sheep, pigs, cows and horses. Wherein the terms "animal" or the plural "animals" are used, it is contemplated that it also applies to any animals.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

As used herein, "administering" or "administration" refers to the process by which the compounds of the present invention are delivered to a subject. The compounds of the present invention may be administered in a variety of ways including, but not limited to, buccally, orally, nasally, or topically. In some embodiments, the compounds are preferably administered topically by transdermal administration. Any of the compounds may also be delivered through encapsulation in vesicles such as extracellular vesicles such as exosomes and microvesicles, liposomes, niosomes, micelles, etc. Topical administration can also involve the use of transdermal administration such as transdermal patches or other acceptable topical carriers. It can also involve the administration of the actives compartmentalized into delivery systems applied to the skin such as a patch, band-aid, strip, film, etc.

The amount of the compound in the drug composition will depend on absorption, distribution, metabolism, and excretion rates of the drug as well as other factors known to those of skill in the art. Dosage values may also vary with the severity of the condition to be alleviated. The compounds may be administered once, or may be divided and administered over intervals of time. It is to be understood that administration may be adjusted according to individual need and professional judgment of a person administrating or supervising the administration of the compounds used in the present invention.

The dose of the compounds administered to a subject may vary with the particular composition, the method of administration, and the particular disorder being treated. The dose should be sufficient to affect a desirable response, such as a therapeutic or prophylactic response against a particular disorder or condition. It is contemplated that one of ordinary skill in the art can determine and administer the appropriate dosage of compounds disclosed in the current invention according to the foregoing considerations.

Dosing frequency for the composition includes, but is not limited to, at least about once every three weeks, once every two weeks, once a week, twice a week, three times a week, four times a week, five times a week, six times a week, or daily. In some embodiments, the interval between each administration is less than about a week, such as less than about any of 6, 5, 4, 3, 2, or 1 day. In some embodiments, the interval between each administration is constant. For example, the administration can be carried out daily, every two days, every three days, every four days, every five days, or weekly. In some embodiments, the administration can be carried out twice daily, three times daily, or more frequent. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between each administration is no more than about a week.

The compounds used in the present invention may be administered individually, or in combination with or concurrently with one or more other compounds used in other embodiments of the present invention. Additionally, compounds used in the present invention may be administered in combination with or concurrently with other therapeutics for inflammation/edema.

The terms "acceptable topical carrier" or "pharmaceutically acceptable topical carrier" encompasses both pharmaceutically-acceptable carriers and cosmetically-acceptable carriers, and it encompasses substantially non-irritating compatible components (either taken alone or in mixtures) which are suitable for delivering the compounds to the skin. The term "compatible", as used herein means that the components of the carrier must be capable of being mixed with a cannabinoid compound and permeation enhancer, in a manner such that there is no interaction which would substantially reduce the efficacy of the composition during use for treating or preventing inflammation/edema in a patient. These carriers must, of course, be of sufficiently high purity and sufficiently low toxicity to render them suitable for chronic topical administration to the skin of humans or lower animals.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention. In the compositions suitable for topical/transdermal administration, the carrier may comprise a penetration enhancing agent and/or a suitable wettable or gelling agent or solvent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g. as a transdermal patch, hydrogel, gel, paste, spot-on, lotion, liquid, spray, cream, or ointment.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; permeation enhancers; releasing agents; sterilizing agents; sweeteners; solubilizers; wetting agents; gelling agents; thickening agents; and mixtures thereof.

The term "compound" as used herein refers to a chemical formulation, either organic or inorganic, which induces a desired pharmacological and/or physiological effect on a subject when administered in a therapeutically effective amount. "Compound" is used interchangeably herein with "drug", "active pharmaceutical ingredient (API)", and "therapeutic agent". In some embodiments, the compound is a cannabinoid.

The term "cannabinoids" as used herein refers to biologically active chemical compounds capable of joining the cannabinoid receptors in a subject's body to produce an effect. Cannabinoids may occur naturally, such as in the *Cannabis sativa, Cannabis indica*, or *Cannabis ruderalis* plant, or may be synthetically created. Exemplary parent cannabinoids include, but are not limited to, Tetrahydrocannabivarin (THCV); Cannabidiol (CBD); Cannabichromene (CBC); Cannabigerol-monomethylether(CBGM); Delta-8-tetrahydrocannabinol(delta 8-THC); Delta-9-tetrahydrocannabinol(THC); Cannabigerol (CBG); Cannabinol (CBN); bibenzyl(−)-cis-perrottetinene (cis-PET) and isomers, enantiomers, derivatives, single and multi-substituted versions, and combinations thereof. Cannabinoids may be natural or synthetic. The term "natural" as used herein refers to a product existing in nature and derivatives thereof. The term "synthetic" or "synthetically derived" as used herein refers to a product produced artificially by human hand by chemical synthesis. In particular, "synthetic" refers to the manufacture of a product which mimics a natural product.

The term "permeation enhancer" or "penetration enhancer" or "chemical enhancer" as used herein refers to compounds and mixtures thereof capable of facilitating skin penetration of drugs and/or enhancing the flux of a drug across the skin. The flux can be increased by changing the resistance (diffusion coefficient) or driving force (gradient for diffusion). Permeation enhancers may be hydrophilic, lipophilic or biphilic. Permeation enhancers may include, but are not limited to, saturated and unsaturated fatty acids, fatty alcohols, alcohols, acetates, monoglycerides, diethanolamides, N,N-dimethylamides, glycols, esters, sulfoxides, terpenes, laurocapram, pyrrolidones, surfactants, bile salts, thiolated polymers, alkyl glycosides, urea, and combinations thereof. Examples of permeation enhancers include, but are not limited to, dimethyl sulfoxide (DMSO), N-Methyl-2- pyrrolidone (NMP), polyethylene glycol (PEG) such as PEG400, lactic acid, oleic acid, palmitic acid, geranic acid, undecanoic acid, geraniol, isopropyl myristate, propyl oleate, glyceryl monooleate, glycerol monolaurate, methyl laurate, lauryl alcohol, lauramide diethanolamide, sorbitan monooleate, sorbitan monolaurate, isopropyl palmitate, limonene, octylpyrrolidone, EDTA, citric acid, sodium salicylates, methoxy salicylates, sodium lauryl sulphate, polyoxyethylene, polyoxyethylene-9-laurylether, polyoxyethylene-20-cetylether, benzalkonium chloride, 23-lauryl ether, cetylpyridinium chloride, cetyltrimethyl ammonium bromide, sodium glycocholate, sodium deoxycholate, sodium taurocholate, sodium glycodeoxycholate, sodium taurodeoxycholate, capric acid, lauric acid, lauric acid/propylene glycol, methyloleate, lysophosphatidylcholine, phosphatidylcholine, cyclodextrins, chitosan-4-thiobutylamide, chitosan-cysteine, poly(acrylic acid)-homocysteine, polycarbophil-cysteine, polycarbophil-cysteine/gsh, chitosan-4-thioethylamide/gsh, chitosan-4-thioglycholic acid, aprotinin, azone, dextran sulfate, menthol, polysorbate 80, and combinations thereof.

"Polymer" as used herein refers to a relatively high molecular weight organic compound, natural or synthetic, whose structure can be represented by a repeated small unit, the monomer. Synthetic polymers are typically formed by addition or condensation polymerization of monomers. Examples of polymers that can be used as herein include, but are not limited to, gelatin, collagen, cellulose ether, and derivatives thereof. Polymers, particularly hydrophilic polymers, may be used herein as a gelling agent for a hydrogel.

The term "hydrophilic polymer" as used herein refers to a synthetic or natural polymer which contain polar or charged functional groups allowing them to dissolve in, or be swollen by, water. In some embodiments, the hydrophilic polymer is capable of being used as a gelling agent or pharmaceutically acceptable carrier for a composition used for topical/transdermal delivery of a hydrophobic compound. In some embodiments, the gelling agent forms a hydrogel. Examples of hydrophilic polymers capable of being used as a gelling agent herein include, but are not limited to, cellulose ether derivatives such as hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), and sodium carboxymethylcellulose (NaCMC); polysaccharides such as dextran, chitosan, and agarose; or proteins such as albumin, gelatin, collagen, lectin, legumine, and viviline. When referring to "gelling agent" herein, it is understood that the gelling agent comprises at least one hydrophilic polymer.

"Hydrogel" as used herein refers to a three-dimensional network of hydrophilic polymers capable of swelling in water and holding a large amount of water while maintaining the structure due to physical or chemical crosslinking of individual polymer chains. Hydrogels have an elastic, jelly-like structure.

"Treatment" or "treating" as used herein refers to any of: the alleviation, amelioration, elimination and/or stabilization of a symptom or characteristic, as well as delay in progression of a symptom of a particular disorder. For example, "treatment" of edema and/or inflammation may include any one or more of the following: amelioration and/or elimination of one or more symptoms/characteristics associated with edema and/or inflammation, reduction of one or more symptoms/characteristics of edema and/or inflammation, stabilization of symptoms/characteristics of edema and/or inflammation, and delay in progression of one or more symptoms/characteristics of edema and/or inflammation.

"Prevention" or "preventing" as used herein refers to any of: halting the effects of edema and/or inflammation, reducing the effects of edema and/or inflammation, reducing the incidence of edema and/or inflammation, reducing the development of edema and/or inflammation, delaying the onset of symptoms of edema and/or inflammation, increasing the time to onset of symptoms of edema and/or inflammation, and reducing the risk of development of edema and/or inflammation.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with inflammation and/or edema. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

Few researchers have worked on improving the systemic absorption of cannabinoids including Jiri et al who patented different CBD formulations including aerosol, emulgel and ointment and evaluated them on human subjects for the treatment of inflammatory diseases (Skalicky, Husek et al. 2012). Jackson et al also patented CBD formulation with no IVPT results (Jackson and Hyatt 2013). Lowe et al formulated and patented transdermal CBD formulation by solubilizing it in volatile oils (*eucalyptus* oil and emu oil) with no in vitro or in vivo data (Tijani, Thakur et al. 2021). Similarly, employment of oils: sunflower, mineral and argan for improving the transdermal delivery of CBD has been reported in the literature (Tijani, Thakur et al. 2021). However, all these studies lack characterization of formulation including flux determination which is important to know the drug permeation profile across the skin after application of the formulation. Lodzki et al developed a reservoir system for transdermal delivery of CBD using ethosomal carriers, in which they achieved ~110.07 µg/cm$^2$ CBD permeation in abdominal skin, ~11.54 µg (g/g muscle) in abdominal muscle and ~0.67 µg/ml concentration in the systemic circulation in their in vivo study in mice (Lodzki, Godin et al. 2003). However, API may leak out from the reservoir patch as reported for fentanyl patch and may affect the systemic absorption of API (Pastore, Kalia et al. 2015). Stinchcomb et al. who developed the cannabinoids solutions in propylene glycol, water and ethanol combination showed flux of Δ8-tetrahydrocannabinol (Δ8-THC), CBD and cannabinol (CBN) in 48 hrs IVPT study. Their IVPT results showed maximum flux of ~1.47 µg/cm$^2$/hr CBD permeation and cumulative amount of ~78.61 µg CBD permeation at the end of 48 hrs (Stinchcomb, Valiveti et al. 2004). Witowski et al patented transdermal encapsulated cannabinoid formulation (patent no. LU101384) in which they achieved flux of 2.7 µg/cm$^2$/hr for CBD formulation in 72 hrs in vivo study (Witowski and Salm 2020). Overall, there is a limited literature available on transdermal delivery of cannabinoids (Tijani, Thakur et al. 2021).

The following non-limiting examples illustrate exemplary compositions and methods of using such compositions in accordance with various embodiments of the disclosure. The examples are merely illustrative and are not intended to limit the disclosure in any way.

Example 1—Composition and Method of Increasing Transdermal Permeation and Flux of Cannabinoids The inventors discovered, using combinational permeation enhancers approach, that they could significantly increase the flux of ~8.50 µg/cm$^2$/hr for CBD, ~6.00 µg/cm$^2$/hr for CBG and ~33.00 µg/cm$^2$/hr for THCV for 0-72 hrs. As noted above, flux for each of the cannabinoids increased to at least about 5.00 µg/cm$^2$/hr, in most cases the increase was at least about 6.00 µg/cm$^2$/hr, which is a significant increase over what has been achieved in the prior art. Drug permeation was shown to be at least about 136 µg/cm$^2$ at 24 hours post administration for CBG and at least about 321 µg/cm$^2$ at 72 hours post administration. Drug permeation for THCV was even higher with at least about 843 g/cm$^2$ drug permeation at 24 hours post administration and at least about 2124 µg/cm$^2$ drug permeation at 72 hours post administration. The inventors are the first to show significantly high transdermal permeation of cannabinoids from a gel formulation using combinational approach of permeation enhancers with significant decrease in inflammation in rat paw in carrageenan induced rat paw edema study (as compared to no treatment group). Although the work focused on three cannabinoids: CBD, THCV and CBG, the formulation approach can be applied to any other minor cannabinoids and result in significant increase in flux.

Results
Pre-Formulation and Formulation

All the cannabinoids including CBD, THCV and CBG showed high solubility in DMSO, NMP, PEG 400 and lactic acid. Further, CBD, THCV and CBG gels were formulated using HEC as a gelling agent. Resultant formulations were transparent in appearance with no precipitation of drug. Drug content assay of CBD, THCV and CBG gels showed 98.23±1.34%, 98.89±0.78% and 97.45±1.76% of drug in all the formulations with no significant drug loss in formulation process.

Rheological Studies

The rheological properties of the gels were assessed. The viscoelasticity data of all sample gels showed non-Newtonian fluid characteristics at room temperature (25° C.). 1% gel formulations of CBD, THCV and CBG demonstrated initial shear thickening characteristics with an infinite shear viscosity plateau observed at higher shear rates.

Differential Scanning Calorimetry (DSC)

Figure 1A:
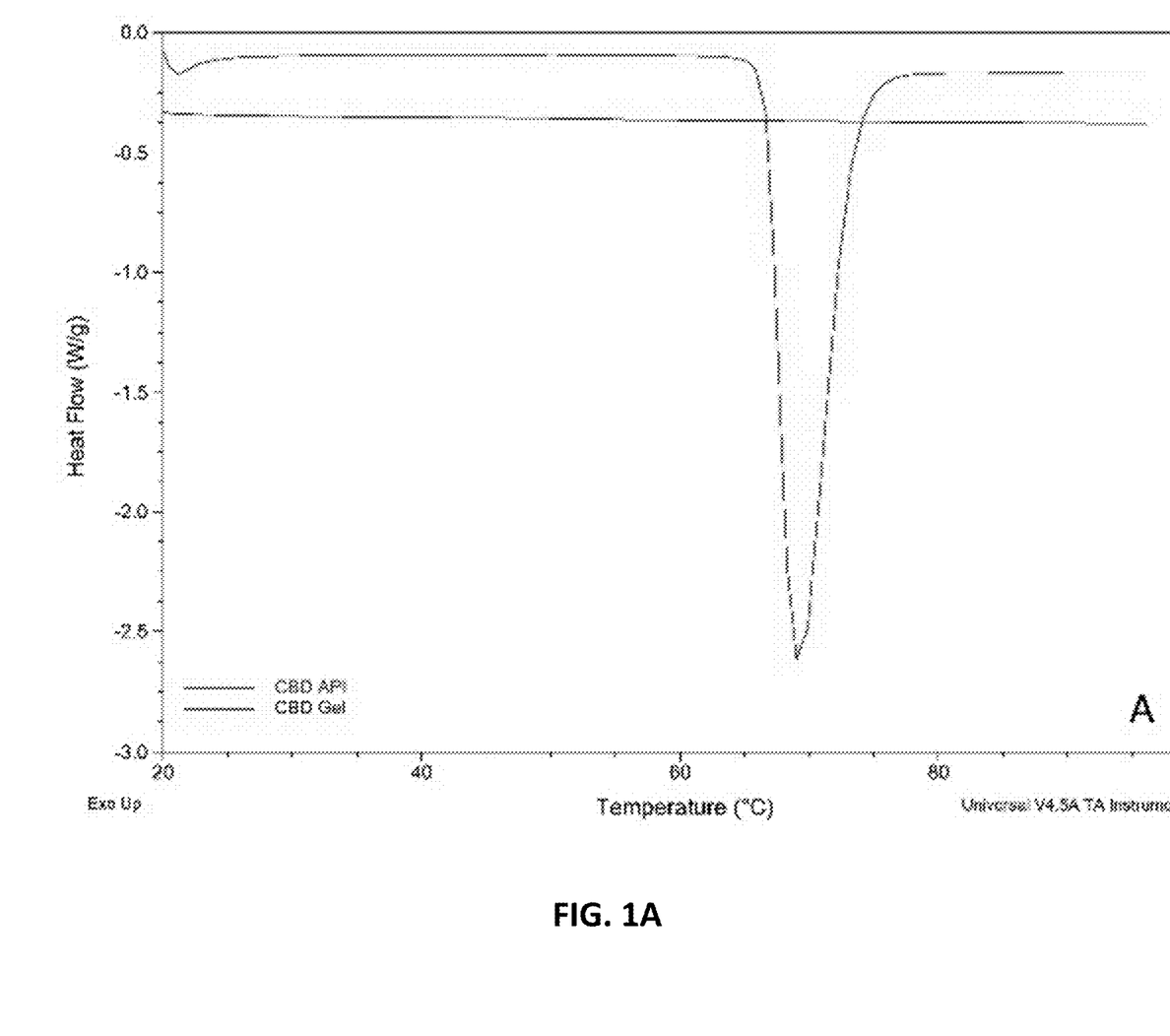
FIG. 1A-C are a series of DSC thermograms of: (A) CBD API and CBD gel, (B) THCV API and THCV gel and (C) CBG API and CBG gel.
Figure 1B:
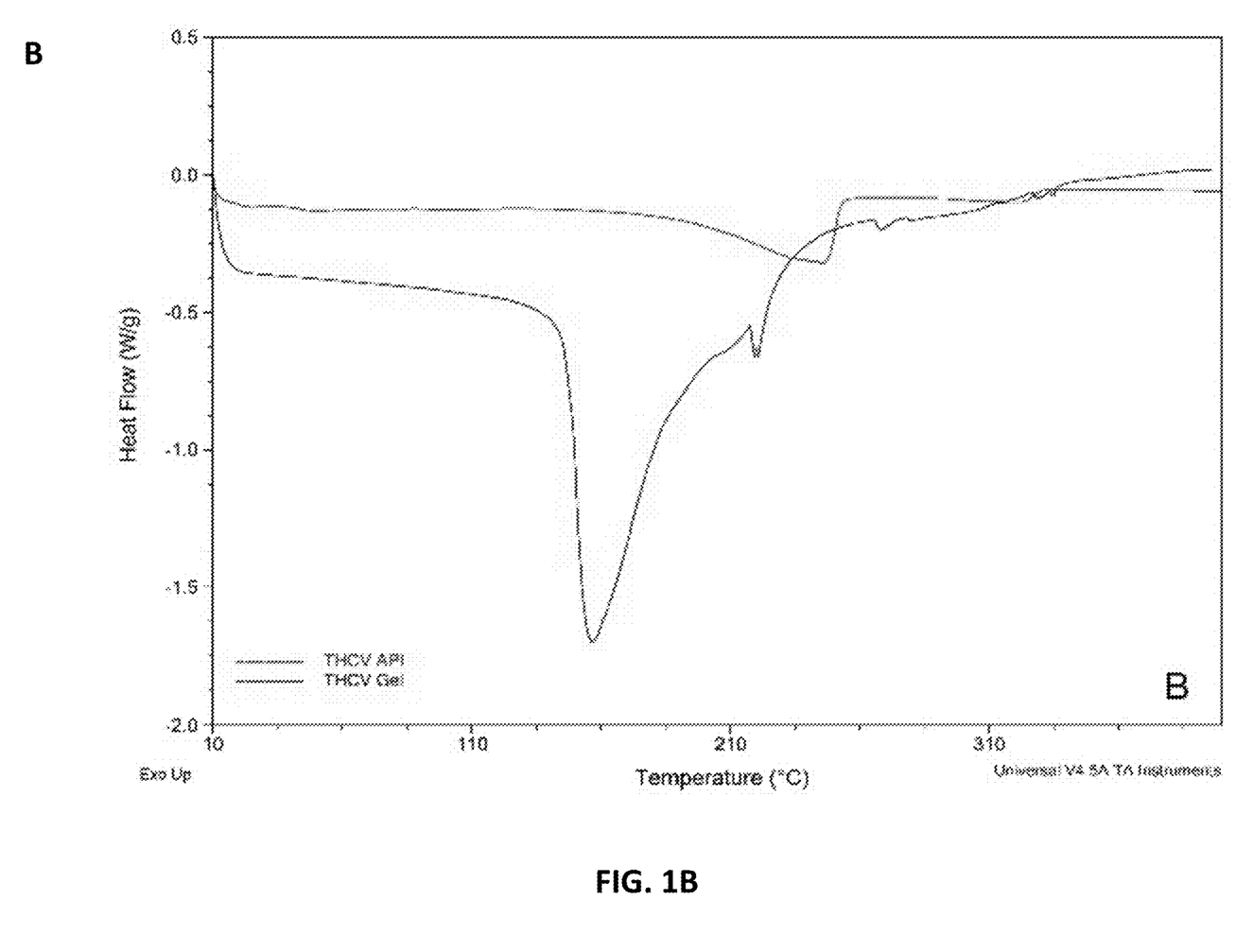
Figure 1C:
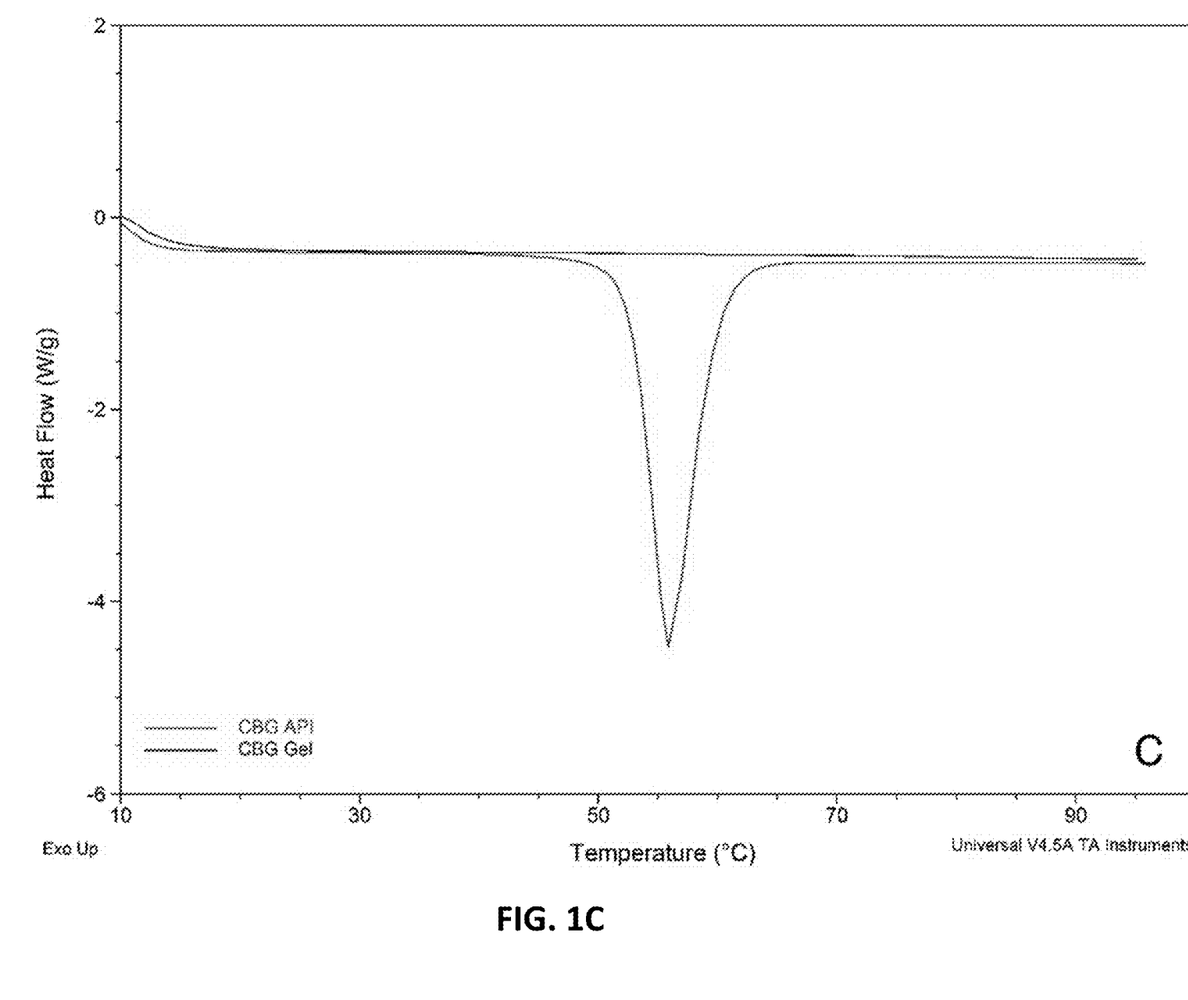

FIG. 1 shows DSC thermograms of CBD, THCV and CBG API as compared to drug mixtures in the gel formulation with DMSO, NMP, PEG400, lactic acid and H.E.C. DSC thermogram of CBD API showed endothermic peak at its melting point 67.5 (° C.), whereas CBD gel formulation thermogram did not show any peak at the melting point temperature of API. DSC thermogram of CBG API also showed endothermic peak at its melting point 56.5 (° C.), whereas CBG gel formulation thermogram did not show any peak at the melting point temperature of API. DSC thermogram of THCV API showed endothermic peak at its melting point 247.5 (° C.), however THCV gel formulation thermogram showed a shifted endothermic peak approximately 100° C. less than the melting point (FIG. 1).

In-Vitro Permeation Testing (IVPT) of CBD Gel Formulation

Figure 2A:
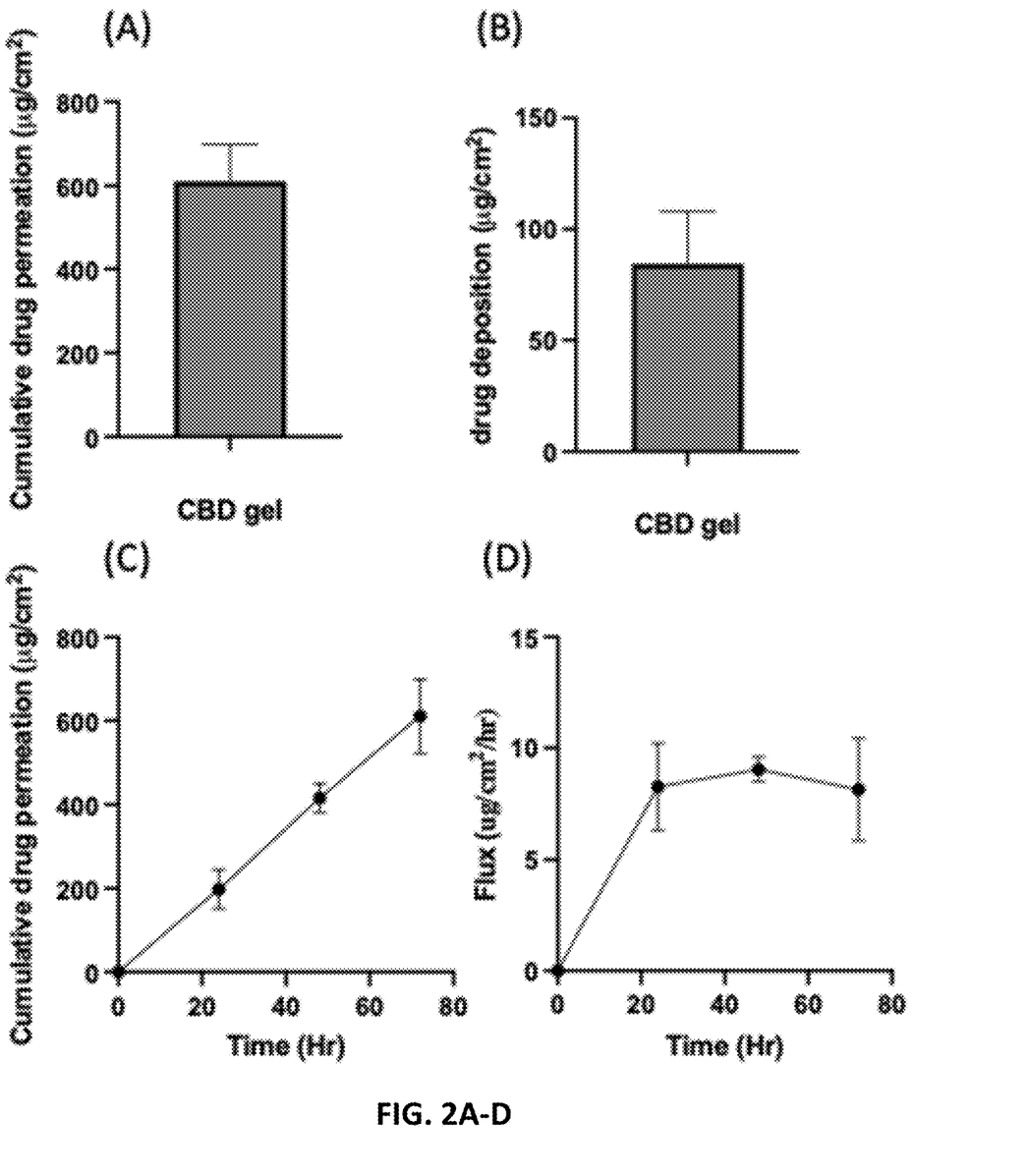

Data showed that 198.40±46.91 µg/cm$^2$, 415.42±34.90 µg/cm$^2$ and 610.96±88.92 µg/cm$^2$ of cumulative CBD was permeated in the receiving media from the gel formulation at 24, 48 and 72 hrs, respectively. Flux was found to be 8.27±1.95 µg/h/cm$^2$, 9.04±0.56 µg/h/cm$^2$ and 8.15±2.30 µg/h/cm$^2$ for 24, 48 and 72 hrs, respectively. Skin deposition study showed that 84.24±23.77 µg/cm$^2$ of CBD was deposited from CBD formulation at the end of 72 hrs study. (FIG. 2).

Effect of Lactic Acid and PEG400 on CBD Permeation

Figures 3A, 3B, 3C, 3D:
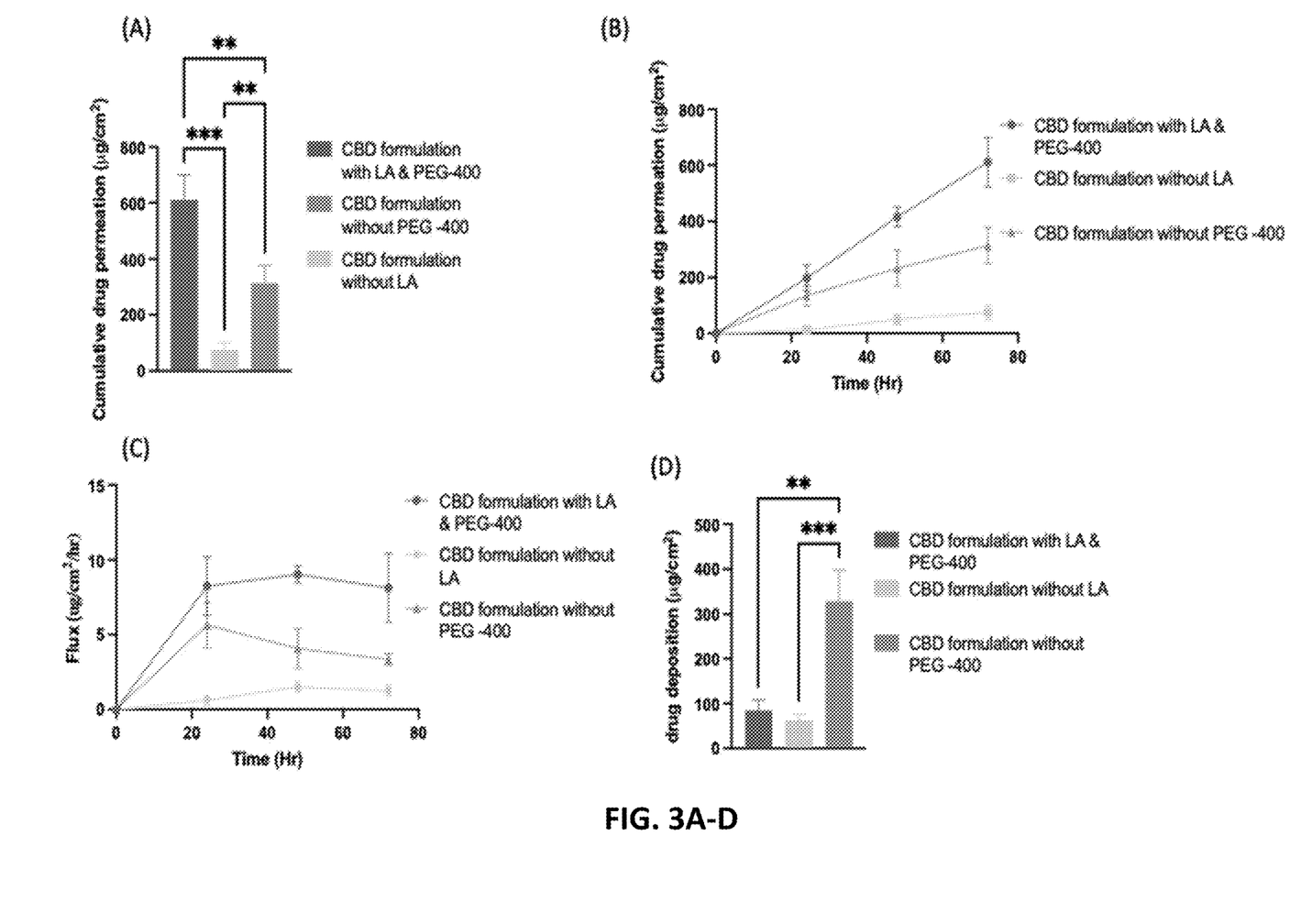

Data showed that CBD formulation with and without lactic acid showed 610.96±88.92 µg/cm$^2$ and 74.80±26.36 µg/cm$^2$ of cumulative drug permeation respectively at the end of 72 hrs study. It was observed that, cumulative drug permeation from a formulation without lactic acid was significantly ($p<0.0001$) decreased by 8.24-fold as compared to gel formulation with lactic acid at the end of 72 hrs IVPT study. Similarly, formulation with lactic acid showed flux of 8.27±1.95 µg/h/cm$^2$, 9.04±0.56 µg/h/cm$^2$ and 8.15±2.30 µg/cm$^2$/hr at 24, 48 and 78 hrs respectively as compared to a formulation without lactic acid which showed flux of 0.62±0.33 µg/cm$^2$/hr, 1.50±0.31 µg/cm$^2$/hr and 1.23±0.37 µg/cm$^2$/hr at 24, 48 and 72 hrs, respectively. Formulation without lactic acid showed 13.33-fold, 6.02-fold and 6.62-fold decrease in flux at 24, 48 and 72 hrs, respectively. Skin deposition study showed that 84.24±23.77 µg/cm$^2$ of CBD was deposited from CBD formulation with lactic acid as compared to formulation without lactic acid which showed 63.08±13.88 µg/cm$^2$ of CBD deposition at the end of 72 hrs study. On the other hand, formulations with PEG400 or without PEG 400 showed 610.96±88.92 µg/cm$^2$ and 313.41±64.53 µg/cm$^2$ of cumulative drug permeation respectively with significant difference at the end of 72 hrs IVPT study. Formulation without PEG-400 showed 1.94-fold decrease in permeation at the end of the study. Formulation without PEG 400 demonstrated a slight elevated flux (5.64±1.54 µg/cm$^2$/hr) at 24 hrs with gradual decrease (3.34±0.37 µg/cm$^2$/hr) at the end of 72 hrs study. Skin deposition study showed that 84.24±23.77 µg/cm$^2$ µg/cm$^2$ of CBD was deposited from CBD formulation with PEG 400 as compared to formulation without PEG 400 which showed 328.51±69.31 µg/cm$^2$ of CBD deposition at the end of 72 hrs study (FIG. 3).

Effect of NMP and DMSO with Water on CBD Permeation

Figure 4A:
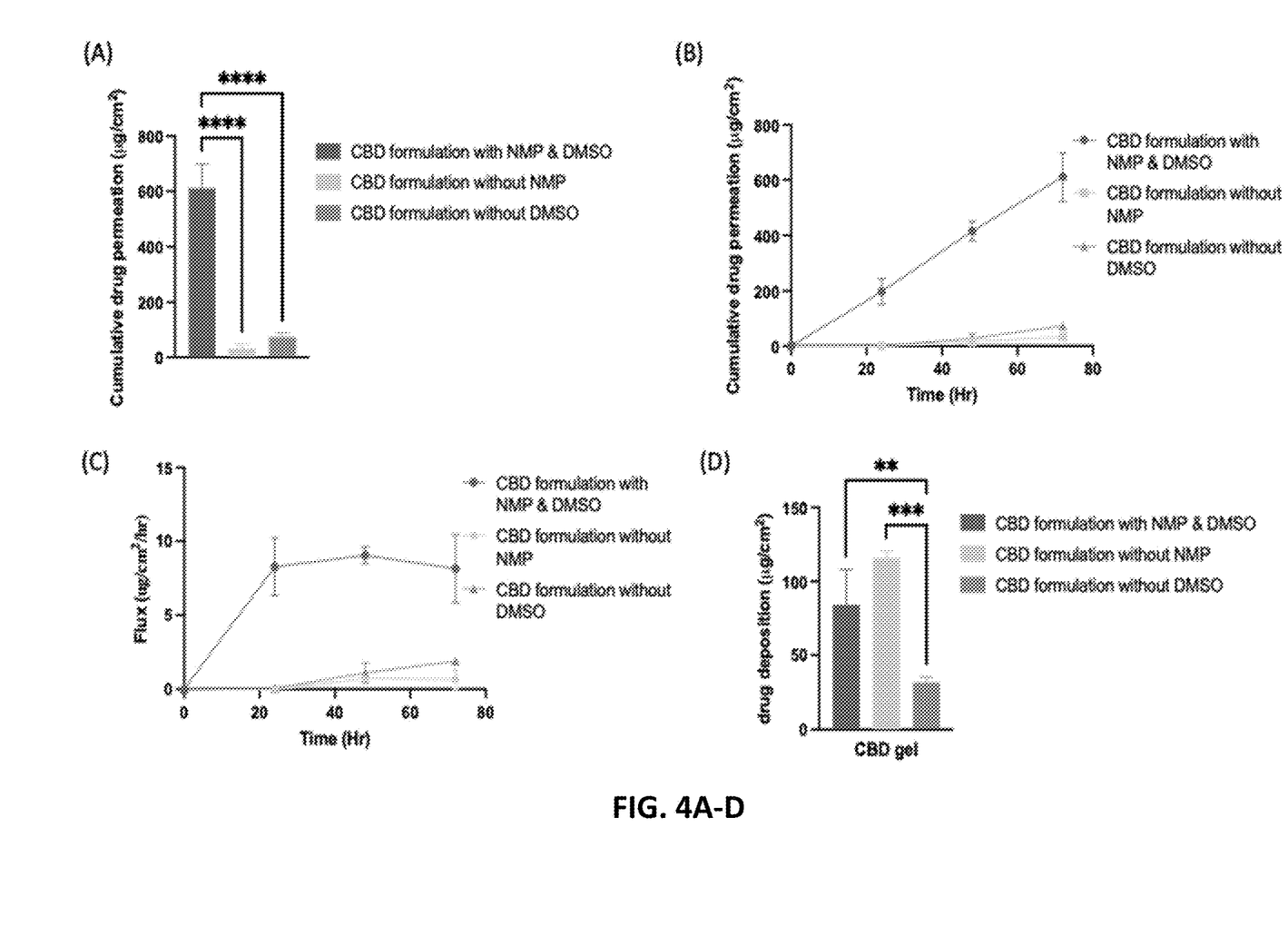

The results revealed that gels with and without NMP showed 610.96±88.92 µg/cm$^2$ and 32.61±14.67 µg/cm$^2$ of cumulative drug permeation respectively at the end of 72 hrs study. It was observed that, cumulative drug permeation from a formulation without NMP was significantly ($p<0.0001$) decreased by 19.06-fold as compared to gel formulation with NMP at the end of 72 hrs IVPT study. Similarly, formulation with NMP showed flux of 8.27±1.95 µg/h/cm$^2$, 9.04±0.56 µg/h/cm$^2$ and 8.15±2.30 µg/h/cm$^2$ at 24, 48 and 72 hrs respectively as compared to a formulation without NMP which showed flux of 0.00±0.00 µg/cm$^2$/hr, 0.70±0.11 µg/cm$^2$/hr and 0.65±0.63 µg/cm$^2$/hr at 24, 48 and 78 hrs, respectively. Skin deposition study showed that 84.24±23.77 µg/cm$^2$ of CBD was deposited from CBD formulation with NMP as compared to formulation without NMP which showed 115.63±4.78 µg/cm$^2$ of CBD deposition at the end of 72 hrs study. Moreover, formulations with or without DMSO showed 610.96±88.92 µg/cm² and 72.76±15.58 µg/cm² of cumulative drug permeation respectively with (p<0.0001) significant difference at the end of 72 hrs IVPT study. Formulation without DMSO demonstrated flux of 1.87±0.18 µg/cm²/hr at the end of 72 hrs study. Skin deposition study showed that 84.24±23.77 µg/cm² of CBD was deposited from CBD formulation with DMSO as compared to formulation without DMSO which showed 31.63±3.82 µg/cm² of CBD deposition at the end of 72 hrs study. In combination with water, formulations without NMP, failed to permeate into the receptor media within the first 24 hrs. (FIG. 4).

Effect of Gelling Concentration on CBD Permeation

Figure 5A:
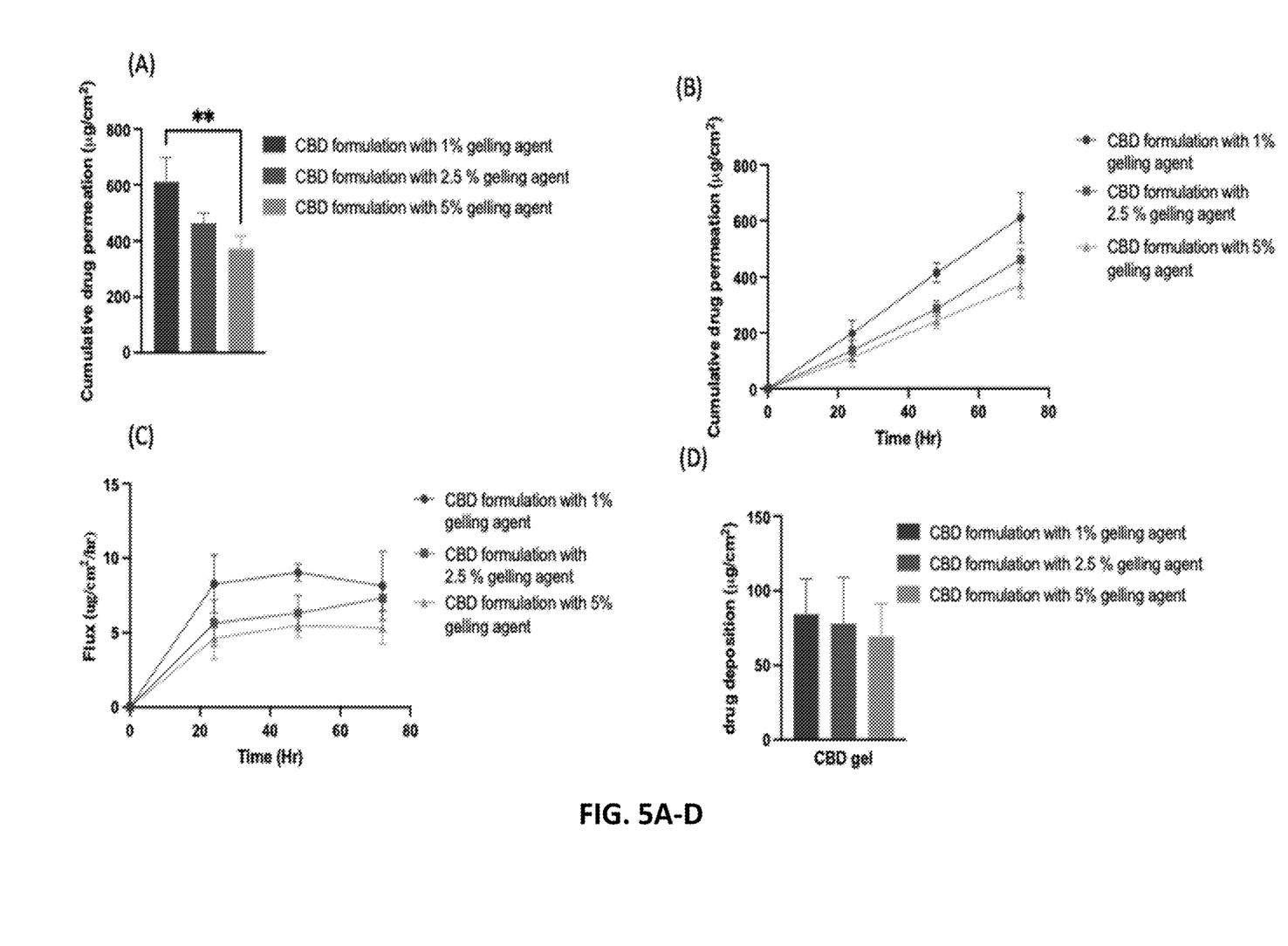

Results revealed that formulation with gelling agent concentration of 1, 2.5 and 5% showed 610.96±88.92 µg/cm², 462.94±35.65 µg/cm² and 371.61±45.11 µg/cm² of cumulative drug permeation, respectively. Gel formulation with 1% gelling agent concentration resulted in increased cumulative drug permeation by 1.32 folds as compared to 2.5 and 1.64-fold as compared to 5% gelling agent concentration. However, there was no significant difference in drug permeation between the groups with 2.5% and 5% gelling agent. Results from skin deposition study showed that 84.24±23.77 µg/cm², 78.06±30.94 µg/cm² and 69.37±21.82 µg/cm² of CBD was deposited from CBD formulation containing 1, 2.5 and 5% gelling agent. (FIG. 5)

IVPT Study of CBG and THCV Gel Formulation

Figure 6A:
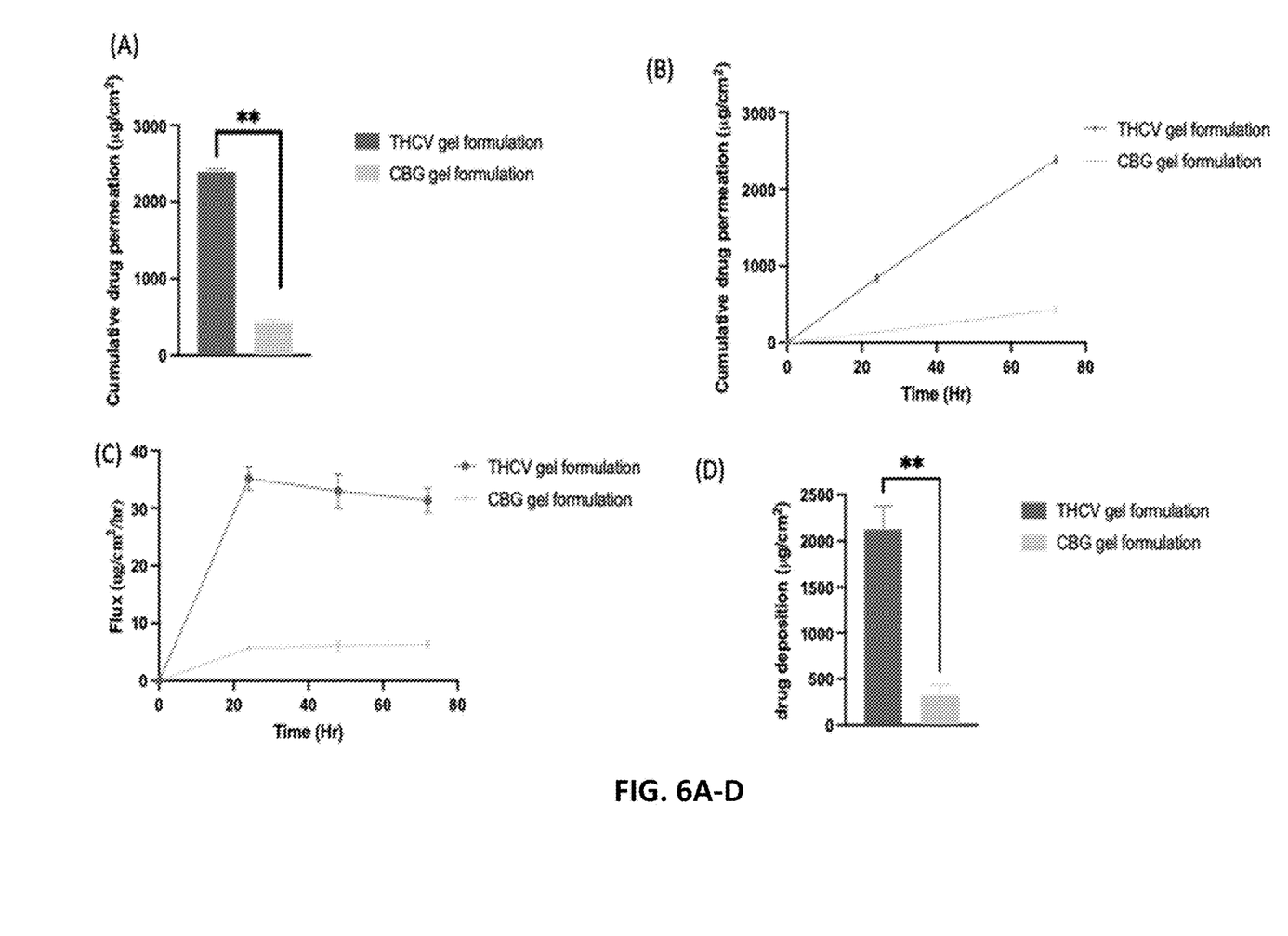

Our skin permeation of CBG results showed that 136.06±0.77 µg/cm², 281.30±20.61 g/cm² and 432.09±35.59 µg/cm² of CBG was permeated in the receiving media from the gel formulation at 24, 48 and 72 hrs, respectively. Further, permeation results of CBG gel formulation showed flux of 5.67±0.03 µg/cm²/hr, 6.05±0.86 µg/cm²/hr and 6.28±0.63 µg/cm²/hr at 24, 48 and 78 hrs, respectively. Skin deposition study showed that 321.91±113.86 µg/cm² of CBG was deposited from CBG formulation at the end of 72 hrs study. Similarly, 843.19±48.98 µg/cm², 1613.19±27.09 µg/cm² and 2384.44±42.22 µg/cm² of cumulative THCV was permeated in the receiving media from the gel formulation at 24, 48 and 72 hrs, respectively. Further, permeation results of THCV gel formulation showed flux of 35.13±2.04 µg/cm²/hr, 32.91±2.92 µg/cm²/hr and 31.30±2.12 µg/cm²/hr at 24, 48 and 78 hrs, respectively. Skin deposition study showed that 2124.40±256.35 µg/cm² of THCV was deposited from initial gel A formulation at the end of 72 hrs study (FIG. 6).

In Vivo Anti-Inflammatory Study in SD Rats

Figure 7:
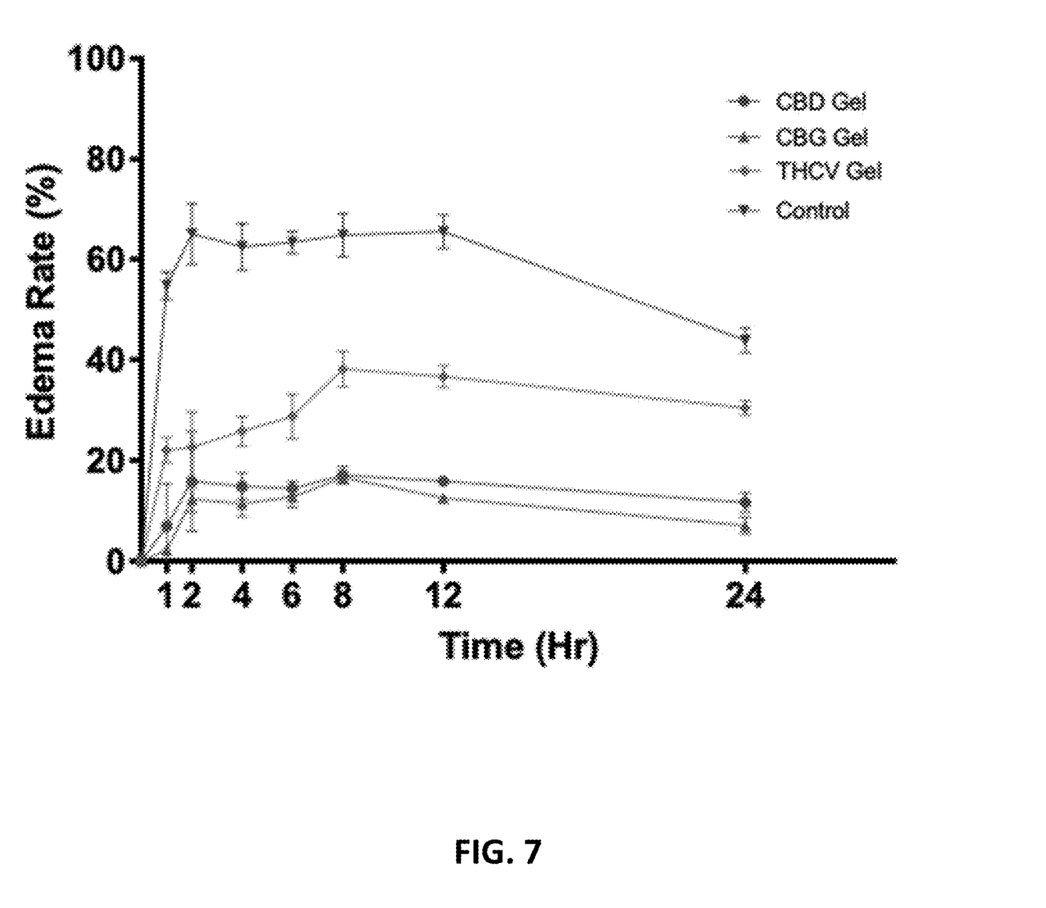
FIG. 7 is a graph depicting inflammatory rate of untreated and treated groups after induction of edema using subplanter injection of carrageenan showing significant reduction in edema after application of CBD, CBG and THCV gel formulations

Administration of carrageenan in rat's paw by sub-planter injection resulted in a time-dependent gradual augmentation of paw volume with maximal values observed between 2-12 h post injection. Edema rates for control (no treatment) group, CBD gel (Gel A), CBG gel (Gel I) and THCV gel (Gel J) were >60.00%, ~21.00%, <20.00% and <20.00% respectively in the first hr of inflammation induction. Results showed that edema rate was reduced by ~4.3-fold, ~5.0-fold and ~1.7-fold as compared to no treatment group at the end of 2 hrs after application of CBD, CBG and THCV gel formulation, respectively. It was also observed that all cannabinoid formulations considerably (p<0.001) reduced paw edema rate at all time points post carrageenan injection as compared to control. CBD and CBG gel applied groups showed the higher anti-inflammatory activity compared to THCV gel (FIG. 7).

Materials and Methods

Materials

CBD and CBG were obtained from Purisys (GA, USA). THCV was obtained from Open books (NC, USA). N-Methyl-2-pyrrolidone (NMP), Dimethyl sulfoxide (DMSO), Polyethylene glycol (PEG) 400, λ-Carrageenan (plant-mucopolysaccharide) and Oleic acid were purchased from Sigma-Aldrich (USA). Lactic Acid was purchased from Merck (Kenilworth, NJ). Hydroxyethyl cellulose (H.E.C.) was purchased from The Dow Chemical Company (Midland, MI). Isopropyl myristate (IPM), Ethyl Oleate and Polyoxyethylene Oleyl Ether were gifts from Croda (Edison, NJ). Transcutol P, Labrasol and Labrafil were gifts from Gattefossé (France).

Pre-Formulation Studies: Solubility of CBD, THCV and CBG

The solubility of APIs including CBD, CBG and THCV was determined in various solvents including dimethyl sulfoxide (DMSO), N-Methyl-2-pyrrolidone (NMP), and PEG 400. Briefly, 100 mg of each API was dissolved in 0.5 ml of DMSO, NMP, PEG400 and vortexed until it dissolved completely. All the solutions were then visually observed for any undissolved particles. Further, all the solubility samples were centrifuged, and the supernatant were collected. Samples were then analyzed using HPLC for the amount of drug solubilized in each solvent.

Cannabinoid Gel Formulation

CBD, THCV and CBG gels (10% w/w) were prepared. Briefly, APIs were weighed and dissolved in dimethyl sulfoxide (DMSO) or N-Methyl-2-pyrrolidone (NMP). PEG400, lactic acid, cosolvents (DMSO or NMP) and penetration enhancers were pipetted appropriately as required. Hydroxy-ethyl cellulose was weighed separately and dissolved in the PEG400/lactic-acid/cosolvent/penetration-enhancer mixture. Drug solutions were transferred into the gel mixture and vortexed for 5 minutes or until

TABLE 1

CBD, CBG and THCV gel formulation with the compositions
Composition (% w/w)

| Components | A | B | C | D | E | F | G | H | I | J |
|---|---|---|---|---|---|---|---|---|---|---|
| CBD | 10 | 10 | 10 | 10 | 10 | 10 | 10 | 10 | | |
| CBG | | | | | | | | | 10 | |
| THCV | | | | | | | | | | 10 |
| DMSO | 43 | 43 | 43 | 43 | — | 43 | 41.5 | 39 | 43 | 43 |
| NMP | 25 | 34 | 41 | — | 25 | 25 | 25 | 25 | 25 | 25 |
| PEG400 | 12 | 12 | — | 12 | 12 | 12 | 12 | 12 | 12 | 12 |
| Lactic Acid | 9 | — | 5 | 9 | 9 | 9 | 9 | 9 | 9 | 9 |
| H.E.C. | 1 | 1 | 1 | 1 | 1 | 1 | 2.5 | 5 | 1 | 1 |
| Water | — | — | — | 25 | 25 | — | — | — | — | — | completely homogenous (Table 1).

Drug Content Assay Using HPLC

All the formulations were analyzed for the drug content using HPLC. HPLC analysis was conducted with a Waters 1525 Binary Pump and a Waters 717plus Autosampler system (Waters Technology Corporation, USA). Methanol/water (85:15 v/v) was used as the mobile phase at a flow rate of 1 mL min-1 with injection volume of 20 uL. Data was only collected from 220 nm channel. A reverse phase C18 column (Symmetry®, 5 μm, 4.6×250 mm; Waters Technology Corporation, USA) with a guard column (Symmetry®, reversed phase, C18) was used for the elution of samples. The retention times were 9.226 mins, 13.13 mins, and 9.713 mins for CBD, THCV and CBG, respectively. The calibration curve (peak area vs concentration) was generated over the range of 2-100 μg/ml and was found to be linear with a correlation coefficient of 0.9998.

Rheology of Topical/Transdermal Hydrogels

Viscosity of the gel formulation was measured using AR 1500 Rheometer (New Castle, DE). Approximately 0.4 mL of gel formulation was loaded onto the lower plate of the rheometer and flow sweep measurements with 0.5 mm gap, 0.1 s-1 to 100 s-1 shear rate and parallel plate geometry (20 mm diameter) were employed in obtaining the viscosity of each formulation. Rheological study was conducted at standard room temperature (25° C.). Results for viscosity were expressed in (Pa-s).

Differential Scanning Calorimetry (DSC)

APIs including CBD, THCV and CBG and their gel formulations were characterized by DSC, (DSCQ100, TA Instruments, New Castle, DE). Data analysis was performed using a thermal analysis software (Universal Analysis 2000, TA Instruments). In general, heating rates of 10° C./min were employed over a temperature range of 10-100° C. for CBD/CBG, and 10-400° C. for THCV. DSC analysis was performed using hermetically sealed pan configuration. CBD, THCV, and CBG or their gel formulations were pre-weighed in an aluminum sample pan for DSC and each measurement was performed in triplicate on different samples (Lodzki, Godin et al. 2003).

In-Vitro Skin Permeation Study

The in-vitro permeation and deposition studies were performed under occlusive conditions using jacketed Franz diffusion cells with a 0.636 cm2 permeation area and 5 mL receptor chamber volume. Human skin used was obtained from The New York Fire Fighter's skin bank and originated from the right and left posterior leg regions. Dermatomed, cryopressed split thickness skin with epidermis and dermis were delivered in plastic bags and stored at −80° C. until further use.

Skin was thawed in water for 45 minutes and was cut into small pieces and mounted on Franz cells. Receptor medium containing PBS with 25% (v/v) ethanol and 5% (v/v) Tween 80 was used for the IVPT study. 0.01% (w/v) sodium azide was added in the receiving media and sonicated for 20 mins to degasify it. To ensure the absence of bubbles in the receptor chamber, each cell was turned upside down to allow release of air though the sampling port. The cells were then left to equilibrate for about 10 mins before application of hydrogel samples. To begin the permeation experiment, 0.2 mL samples of each formulation was pipetted onto the donor compartment. The donor compartment of each cell was sealed with parafilm and perforated with a needle and the fastened to the receiving compartment using a clamp. Following the completion of the experimental setup, the Franz diffusion cells were blanketed to prevent photo-degradation of samples and the system kept at 32.3° C. with the use of its circulating water bath to maintain the skin surface temperature of 32° C. throughout the duration of the experiment. A 72 hr experimentation duration was employed with sampling times set at 24 hr increments. 1 mL samples were withdrawn from the receptor chamber via the sampling port and analyzed by HPLC, and the entire remaining receiving media in the receptor chamber was discarded and replaced with a fresh batch. The cumulative amount of drug permeated through the skin per unit area ($Q_p$) was calculated from drug concentration in the receptor fluid and plotted as a function of time. The steady-state flux (J) was determined as the slope of the linear portion of the plot.

In-Vitro Skin Deposition Study

Upon completion of the in-vitro permeation experiment, the residue hydrogel samples on each skin were carefully wiped off with ethanol/water (50:50) solution and the skin treated further to remove the unabsorbed drugs. Subsequently, the skin samples were removed from the Franz diffusion cells and the area exposed to the donor compartment and receiving compartment of the cells were excised, thinly sliced into fine sections, and placed into a 1 mL solution of methanol/RM (50:50). Each 1 mL suspension was vortexed for 1-2 mins, soaked in a sonicator for 1 hr and centrifuged at 14000 rpm at 24° C. for 15 mins. After centrifugation, the 0.2 mL of the supernatant was collected and placed in vials for HPLC analysis. The deposited drug amounts ($Q_{d,72}$) were expressed as micrograms per unit area of the excised skin with average results expressed from experiments conducted with at least three sample groups.

Carrageenan-Induced Acute Inflammatory Model

The anti-inflammatory effect of the gel formulations was assessed using carrageenan-induced paw edema model (Whiteley and Dalrymple 1998, Lee and Crosby 1999, Sammons, Raval et al. 2000, Cong, Khaziakhmetova et al. 2015) using Sprague Dawley (SD) rats. This model was deduced suitable for the evaluation of anti-inflammatory and anti-hyperalgesic drugs (Whiteley and Dalrymple 1998, Lee and Crosby 1999, Sammons, Raval et al. 2000, Cong, Khaziakhmetova et al. 2015). Edema was induced in male Sprague Dawley (SD) rats by sub-plantar injection of 50 μL of 0.1% λ-carrageenan (22049 SIGMA λ-Carrageenan plant-mucopolysaccharide, Sigma-Aldrich) gel in nuclease free water into the left hind paw of the animals. The inventors evaluated the intensity, development, and duration of the induced inflammation by measurements of rat paw volume using a digital plethysmometer (LE 7500, Panlab, Harvard Apparatus). Measurements were made prior to edema induction (base-line volume) and at 1, 2, 4, 6, 8, 12, and 24 hrs after sub-plantar carrageenan injection. The intensity of inflammation was assessed by calculating the percentage of increase in paw volume against the base-line measurements. Animals were divided into 4 groups of 4 rats each; group 1: control (no treatment); group 2: CBD gel (Gel A); group 3: CBG gel (Gel I); and group 4: THCV gel (Gel J). The preliminary studies showed that placebo gels (without CBD or CBG or THCV) didn't show reduction in edema as compared to control group (No treatment with gel) in pharmacodynamic experiments in vivo which is consistent with other studies the inventors have conducted in the past (Bagde, Patel et al. 2019). Therefore, placebo gels were not considered in the study.

Statistical Analysis

Tests for significant differences among means were performed using the one-way analysis of variance (ANOVA) accompanied by Tukey and Dunnett post-analysis tests. Differences between groups were considered significant at the p<0.05 level. Statistical analyses were performed with GraphPad Prism 5.0 (GraphPad Software, Inc., San Diego, CA).

CONCLUSION

The inventors have successfully developed a gel formulation having high transdermal permeation of cannabinoids. The novel formulation exhibited significant decrease in inflammation in vivo as compared to the control.

Example 2—Method of Treating Inflammation/Edema in a Patient with CBD (Prophetic)

A 20-year-old man presents with edema and inflammation of the skin on his forearm. The patient is topically administered a therapeutically effective amount of a composition comprised of CBD (10% w/w) as well as a combination of permeation enhancers of PEG400, LA, NMP, and DMSO in a gel containing HEC a for a time period sufficient to alleviate his symptoms. The symptoms do not return.

The gel is prepared with CBD (10% w/w) being weighed and dissolved in dimethyl sulfoxide (DMSO) or N-Methyl-2-pyrrolidone (NMP) to form a drug solution. PEG400 (12% w/w), lactic acid (9% w/w), DMSO (43% w/w) and NMP (25% w/w) are mixed to form a penetration enhancer mixture. Hydroxy-ethyl cellulose (1% w/w) is weighed separately and dissolved in the penetration enhancer mixture to form a gel mixture. Drug solutions are transferred into the gel mixture and vortexed for 5 minutes or until completely homogenous.

Example 3—Method of Treating Inflammation/Edema in a Patient with CBG (Prophetic)

A 29-year-old woman presents with edema and inflammation of the skin on her leg. The patient is topically administered a therapeutically effective amount of a composition comprised of CBG (10% w/w) as well as a combination of permeation enhancers of PEG400, LA, NMP, and DMSO in a gel containing HEC a for a time period sufficient to alleviate her symptoms. The symptoms do not return.

The gel is prepared with CBG (10% w/w) being weighed and dissolved in dimethyl sulfoxide (DMSO) or N-Methyl-2-pyrrolidone (NMP) to form a drug solution. PEG400 (12% w/w), lactic acid (9% w/w), DMSO (43% w/w) and NMP (25% w/w) are mixed to form a penetration enhancer mixture. Hydroxy-ethyl cellulose (1% w/w) is weighed separately and dissolved in the penetration enhancer mixture to form a gel mixture. Drug solutions are transferred into the gel mixture and vortexed for 5 minutes or until completely homogenous.

Example 4—Method of Treating Inflammation/Edema in a Patient with THCV (Prophetic)

A 50-year-old man presents with edema and inflammation of the skin on his forearm. The patient is topically administered a therapeutically effective amount of a composition comprised of THCV (10% w/w) as well as a combination of permeation enhancers of PEG400, LA, NMP, and DMSO in a gel containing HEC a for a time period sufficient to alleviate his symptoms. The symptoms do not return.

The gel is prepared with THCV (10% w/w) being weighed and dissolved in dimethyl sulfoxide (DMSO) or N-Methyl-2-pyrrolidone (NMP). PEG400 (12% w/w), lactic acid (9% w/w), DMSO (43% w/w) and NMP (25% w/w) are mixed to form a penetration enhancer mixture. Hydroxy-ethyl cellulose (1% w/w) is weighed separately and dissolved in the penetration enhancer mixture to form a gel mixture. Drug solutions are transferred into the gel mixture and vortexed for 5 minutes or until completely homogenous.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described.

What is claimed is:

1. A method of treating inflammation or edema in a patient in need thereof comprising:
    administering a therapeutically effective amount of a gel composition to the patient in need thereof, the composition comprising
        at least one cannabinoid present in the composition at a concentration of between about 1% (w/w) to about 15% (w/w);
        a combination of permeation enhancers each present in the composition at a concentration of between about 9% (w/w) to about 43% (w/w) wherein the combination of permeation enhancers comprises lactic acid (LA), polyethylene glycol-400 (PEG-400), N-methyl-2 pyrrolidone (NMP), and dimethyl sulfoxide (DMSO); and
        at least one hydrophilic polymer present in the composition at a concentration of between about 1% (w/w) to about 5% (w/w) wherein the at least one hydrophilic polymer is selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof;
    wherein the administration of the composition treats the inflammation or edema of the patient.

2. The method of claim 1, wherein the at least one cannabinoid is selected from the group consisting of Tetrahydrocannabivarin (THCV), Cannabidiol (CBD), Cannabichromene (CBC), Cannabigerol-monomethylether (CBGM), Delta-8-tetrahydrocannabinol (delta 8-THC), Delta-9-tetrahydrocannabinol (THC), Cannabigerol (CBG), Cannabinol (CBN), bibenzyl (−)-cis-perrottetinene (cis-PET), and combinations thereof.

3. The method of claim 2, wherein the at least one cannabinoid is CBD, CBG, or THCV.

4. The method of claim 1, wherein the LA is present in the composition at a concentration of about 9% (w/w), the PEG-400 is present in the composition at a concentration of about 12% (w/w), the NMP is present in the composition at about 25% (w/w) and the DMSO is present in the composition at about 43% (w/w).

5. The method of claim 1, wherein the at least one hydrophilic polymer is HEC.

6. A gel composition for treating inflammation in a patient in need thereof comprising:
   at least one cannabinoid present in the composition at a concentration of between about 1% (w/w) to about 15% (w/w);
   a combination of permeation enhancers each present in the composition at a concentration of between about 9% (w/w) to about 43% (w/w) wherein the combination of permeation enhancers comprises lactic acid (LA), polyethylene glycol-400 (PEG-400), N-methyl-2 pyrrolidone (NMP), and dimethyl sulfoxide (DMSO); and
   at least one hydrophilic polymer present in the composition at a concentration of between about 1% (w/w) to about 5% (w/w) wherein the at least one hydrophilic polymer is selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof.

7. The composition of claim 6, wherein the at least one cannabinoid selected from the group consisting of Tetrahydrocannabivarin (THCV), Cannabidiol (CBD), Cannabichromene (CBC), Cannabigerol-monomethylether (CBGM), Delta-8-tetrahydrocannabinol (delta 8-THC), Delta-9-tetrahydrocannabinol (THC), Cannabigerol (CBG), Cannabinol (CBN), bibenzyl (−)-cis-perrottetinene (cis-PET), and combinations thereof.

8. The composition of claim 7, wherein the at least one cannabinoid is CBD, CBG, or THCV.

9. The composition of claim 6, wherein the LA is present in the composition at a concentration of about 9% (w/w), the PEG-400 is present in the composition at a concentration of about 12% (w/w), the NMP is present in the composition at about 25% (w/w) and the DMSO is present in the composition at about 43% (w/w).

10. The composition of claim 6, wherein the at least one hydrophilic polymer is HEC.

11. A method of increasing transdermal permeation of at least one cannabinoid through a skin of a patient in need thereof comprising:
   administering a therapeutically effective amount of a gel composition to the patient in need thereof, the composition comprising
      at least one cannabinoid present in the composition at a concentration of between about 1% (w/w) to about 15% (w/w);
      a combination of permeation enhancers each present in the composition at a concentration of between about 9% (w/w) to about 43% (w/w) wherein the combination of permeation enhancers comprises lactic acid (LA), polyethylene glycol-400 (PEG-400), N-methyl-2 pyrrolidone (NMP), and dimethyl sulfoxide (DMSO); and
      at least one hydrophilic polymer present in the composition at a concentration of between about 1% (w/w) to about 5% (w/w) wherein the at least one hydrophilic polymer is selected from the group consisting of hydroxyethyl cellulose (HEC), methylcellulose (MC), ethylcellulose (EC), hydroxypropyl cellulose (HPC), hydroxyethyl methylcellulose (HEMC), hydroxypropyl methylcellulose (HPMC), sodium carboxymethylcellulose (NaCMC), and combinations thereof;
   wherein flux of the at least one cannabinoid is increased above a control within about 72 hours after administration of the composition wherein the flux is increased to at least about 5.00 $\mu g/cm^2/hr$;
   wherein the increase in the flux increases the transdermal permeation of the at least one cannabinoid.

12. The method of claim 11, wherein the at least one cannabinoid is selected from the group consisting of Tetrahydrocannabivarin (THCV), Cannabidiol (CBD), Cannabichromene (CBC), Cannabigerol-monomethylether (CBGM), Delta-8-tetrahydrocannabinol (delta 8-THC), Delta-9-tetrahydrocannabinol (THC), Cannabigerol (CBG), Cannabinol (CBN), bibenzyl (−)-cis-perrottetinene (cis-PET), and combinations thereof.

13. The method of claim 12, wherein the at least one cannabinoid is CBD, CBG, or THCV.

14. The method of claim 11, wherein the LA is present in the composition at a concentration of about 9% (w/w), the PEG-400 is present in the composition at a concentration of about 12% (w/w), the NMP is present in the composition at about 25% (w/w) and the DMSO is present in the composition at about 43% (w/w).

* * * * *